(12) United States Patent  
Verstappen et al.

(10) Patent No.: US 7,630,087 B2
(45) Date of Patent: Dec. 8, 2009

(54) INSPECTION METHOD AND APPARATUS, LITHOGRAPHIC APPARATUS, LITHOGRAPHIC PROCESSING CELL AND DEVICE MANUFACTURING METHOD

(75) Inventors: Leonardus Henricus Marie Verstappen, Weert (NL); Antoine Gaston Marie Kiers, Veldhoven (NL); Goce Naumoski, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 224 days.

(21) Appl. No.: 11/603,257

(22) Filed: Nov. 22, 2006

(65) Prior Publication Data

US 2008/0117434 A1    May 22, 2008

(51) Int. Cl.
    *G01B 11/24* (2006.01)
(52) U.S. Cl. .............. 356/601; 356/237.1; 356/237.6; 356/609
(58) Field of Classification Search ... 356/237.1–237.6, 356/601, 604, 607–609, 239.8, 239.7, 521
See application file for complete search history.

(56) References Cited

U.S. PATENT DOCUMENTS

| 5,703,692 | A | 12/1997 | McNeil et al. ............. 356/445 |
| 5,880,838 | A | 3/1999 | Marx et al. ................. 356/351 |
| 5,963,329 | A | 10/1999 | Conrad et al. .............. 356/372 |
| 6,559,953 | B1 * | 5/2003 | Davids ....................... 356/521 |
| 6,608,690 | B2 | 8/2003 | Niu et al. .................... 356/635 |
| 6,699,624 | B2 | 3/2004 | Niu et al. ....................... 430/5 |
| 6,704,661 | B1 | 3/2004 | Opsal et al. ................... 702/27 |
| 6,721,691 | B2 | 4/2004 | Bao et al. .................... 702/189 |
| 6,738,138 | B2 | 5/2004 | Wei ............................. 356/369 |
| 6,753,961 | B1 | 6/2004 | Norton et al. ............... 356/364 |
| 6,768,983 | B1 | 7/2004 | Jakatdar et al. ............... 706/46 |
| 6,772,084 | B2 | 8/2004 | Bischoff et al. ............. 702/127 |
| 6,785,638 | B2 | 8/2004 | Niu et al. .................... 702/189 |
| 6,813,034 | B2 | 11/2004 | Rosencwaig et al. ........ 356/601 |
| 6,819,426 | B2 | 11/2004 | Sezginer et al. ............. 356/401 |
| 6,856,408 | B2 | 2/2005 | Raymond ................... 356/601 |
| 6,919,964 | B2 | 7/2005 | Chu ............................ 356/601 |
| 6,928,628 | B2 | 8/2005 | Seligson et al. ................ 716/4 |

(Continued)

FOREIGN PATENT DOCUMENTS

EP     1 628 164 A2    2/2006

(Continued)

*Primary Examiner*—Gregory J Toatley, Jr.
*Assistant Examiner*—Iyabo S Alli
(74) *Attorney, Agent, or Firm*—Sterne, Kessler, Goldstein & Fox P.L.L.C.

(57) ABSTRACT

Measurement of a profile of a scatterometry object on top of one or more product layers on a substrate is disclosed. To prevent an unknown parameters of one or more product layers having an effect on the measurement of the object profile, the thickness of the one or more product layers is measured prior to measuring the profile of the scatterometry object on the layer(s). In an embodiment, each of a plurality of product layers is measured as it is exposed so that only the degree of freedom of the most recently exposed product layer is unknown at each measurement step. When each of a plurality of product layers has been measured, and a scatterometry object is placed at the top of the layers, only the degrees of freedom of that scatterometry object should be unknown and only the profile of the object should need to be measured.

16 Claims, 4 Drawing Sheets

U.S. PATENT DOCUMENTS

| | | | | |
|---|---|---|---|---|
| 6,972,852 B2 | 12/2005 | Opsal et al. | ................. | 356/625 |
| 6,974,962 B2 | 12/2005 | Brill et al. | ................... | 250/548 |
| 6,987,572 B2 | 1/2006 | Lakkapragada et al. | ..... | 356/601 |
| 7,046,376 B2 | 5/2006 | Sezginer | .................... | 356/601 |
| 7,061,615 B1 | 6/2006 | Lowe-Webb | ................ | 356/401 |
| 7,061,623 B2 | 6/2006 | Davidson | .................... | 356/497 |
| 7,061,627 B2 | 6/2006 | Opsal et al. | ................. | 356/601 |
| 7,068,363 B2 * | 6/2006 | Bevis et al. | .............. | 356/237.5 |
| 7,411,207 B2 * | 8/2008 | Nishiyama et al. | ....... | 356/237.1 |
| 2003/0028358 A1 | 2/2003 | Niu et al. | ....................... | 703/2 |
| 2004/0119970 A1 | 6/2004 | Dusa et al. | ............... | 356/237.1 |
| 2006/0033921 A1 | 2/2006 | Den Boef et al. | ........... | 356/446 |
| 2006/0066855 A1 | 3/2006 | Den Boef et al. | ........... | 356/401 |
| 2006/0126074 A1 | 6/2006 | Van Der Werf et al. | ...... | 356/489 |
| 2006/0139592 A1 | 6/2006 | Den Boef et al. | ........... | 355/53 |

FOREIGN PATENT DOCUMENTS

EP        1 628 164 A3     4/2006

* cited by examiner

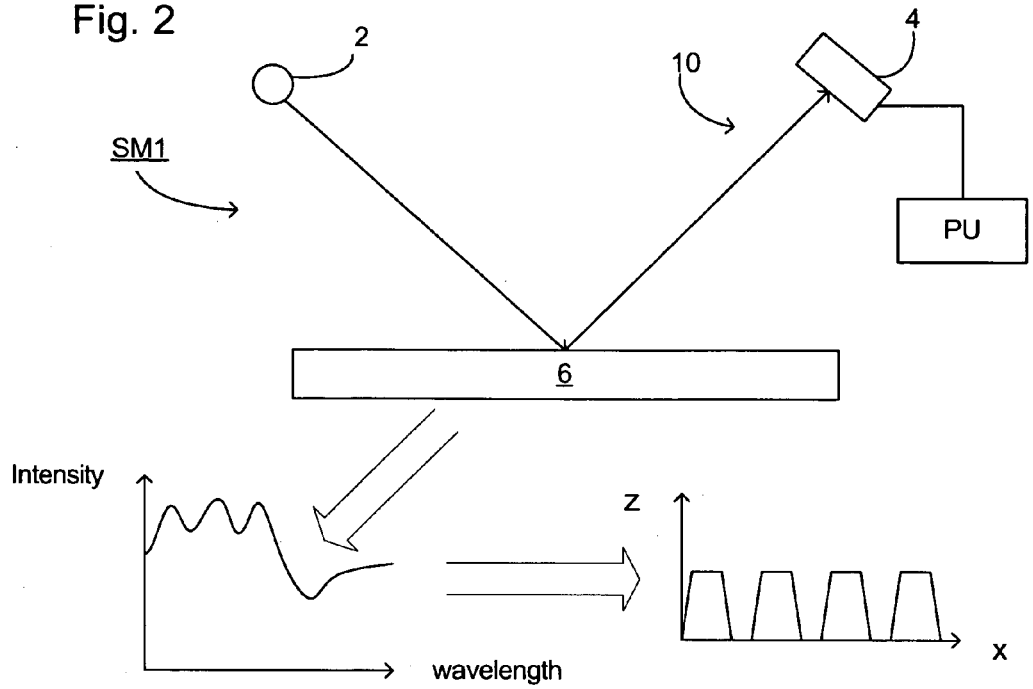
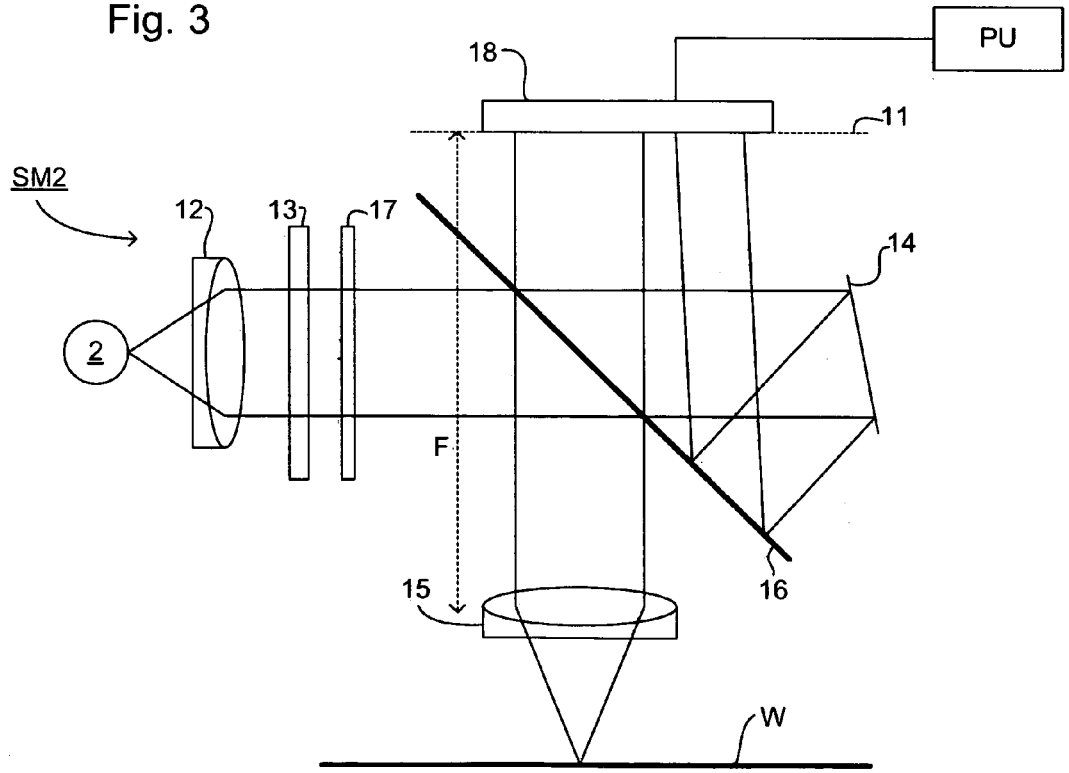

INSPECTION METHOD AND APPARATUS, LITHOGRAPHIC APPARATUS, LITHOGRAPHIC PROCESSING CELL AND DEVICE MANUFACTURING METHOD

FIELD

The present invention relates to a method of inspection usable, for example, in the manufacture of devices by a lithographic technique and to a method of manufacturing devices using a lithographic technique.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, one or more parameters of the patterned substrate are typically measured, for example the overlay error between successive layers formed in or on the substrate. There are various techniques for making measurements of the microscopic structures formed in a lithographic process, including the use of a scanning electron microscope and various specialized tools. One form of specialized inspection tool is a scatterometer in which a beam of radiation is directed onto a target on the surface of the substrate and one or more properties of the scattered or reflected beam are measured. By comparing one or more properties of the beam before and after it has been reflected or scattered by the substrate, one or more properties of the substrate may be determined. This may be done, for example, by comparing the reflected beam with data stored in a library of known measurements associated with a known substrate property. Two main types of scatterometer are known. A spectroscopic scatterometer directs a broadband radiation beam onto the substrate and measures the spectrum (intensity as a function of wavelength) of the radiation scattered into a particular narrow angular range. An angularly resolved scatterometer uses a monochromatic radiation beam and measures the intensity of the scattered radiation as a function of angle. An ellipsometer also measures polarization state.

In order that the radiation that impinges on the substrate is diffracted, an object with a specific profile and pitch is printed on to the substrate and is often known as a scatterometry object or scatterometry profile. The object may be a diffraction grating or the like, which is made up of an array of bars or other periodic structures. The cross-section of the structures, as seen from the surface of the substrate upwards, is known as the profile. Ideally, the object (or a plurality of different objects) that is printed on to the substrate would have a predetermined shape and would be printed perfectly each time it was printed. However, because of the small size (ranging from, for example, 32 to 250 nm) of the object, its size is very sensitive to processing variations of all types. Accordingly, it is desirable to have a system to determine how exactly the object is shaped, i.e., know the profile of the object.

Generally, the way in which the profile of a scatterometry object may be determined is by diffracting a beam of radiation from the object and comparing the diffraction pattern with model diffraction patterns that are stored in a library of diffraction patterns alongside the model profiles that create these model patterns. For example, United States patent application publication US 2003/0028358 describes a system in which an actual signal from a scatterometry object is compared with a library of stored signals and the system tries to find the closest match of signals. The stored signals are each linked to an object profile parameter. An object profile parameter may be, for instance, the critical dimension (CD), a width of the object (which may vary with height), the height of the object or the angle of a side surface of the object (this angle being measured either from the surface of the substrate or from a normal to the substrate surface). It then goes on to describe the method of finding a closest match of a signal with each parameter of the scatterometry object. In other words, various possible parameters and possible permutations of parameters are tested to find a combination that gives rise to a signal that is as close as possible to the actual signal that has come from the scatterometry object. This gives a series of iterations of a "model signal". This method is repeated iteratively until the model signal is as close as possible to the actual signal and then the model signal is stored alongside the parameters used. Finally, a computer checks the database comprising the parameters to determine if all parameter combinations have been entered.

SUMMARY

There are cases in which the scatterometry object is printed onto an existing product layer on the substrate. The product layer may be a printed layer or it may be a homogeneous layer. When measuring the profile of an object that is printed on top of a stack of product layers, the thicknesses of the product layers will affect the diffracted beam. To measure the complete stack, taking into account all of the properties of all of the layers in the stack is a difficult and sometimes even impossible mathematical problem. For instance, there may be too many degrees of freedom (or too many variable parameters) that may lead to corresponding variations in a measurement signal received from the surface of the stack. It is therefore desirable to minimize and preferably eliminate the number of degrees of freedom brought into the reconstruction equation by any product layers.

When there are product layers beneath the printed object layer, the thickness of the product layers provides a further parameter or further degree of freedom which is not taken in to account in United States patent application publication US 2003/0028358 A1. Each degree of freedom provides a further possibility of cross-correlations between parameters or degrees of freedom and therefore an increased probability of erroneous results.

It is desirable, for example, to provide a method of reconstructing a shape of an object from a diffraction pattern resulting from radiation illuminating the object, the method comprising:

measuring a thickness of a product layer on a substrate;

using the measured thickness to estimate an object position relative to the substrate, the object positioned on the product layer;

detecting the diffraction pattern of radiation diffracted from the object;

estimating the object shape;

deriving a model diffraction pattern from the estimated shape taking into account the estimated object position;

comparing the model diffraction pattern and the detected diffraction pattern; and determining the actual shape of the object from the difference between the model diffraction pattern and the detected diffraction pattern.

According to an aspect of the invention, there is provided an inspection apparatus configured to measure a property of a substrate, the apparatus comprising:

a detector configured to detect an actual spectrum signal associated with an object on the substrate;

a controller configured to select a first model profile based on a plurality of variable and non-variable parameters of the model profile from a library;

a generator configured to generate a first spectrum signal associated with the first model profile; and a comparator configured to compare the first spectrum signal with the actual spectrum signal, wherein if the first spectrum signal and the actual spectrum signal do not match to within a desired tolerance, the generator and comparator are configured to carry out their respective generation and comparison with a second model profile having varied variable profiles with respect to the first model profile, wherein the inspection apparatus is configured to measure a parameter of a product layer on the substrate, and to use the measured parameter to estimate an object position relative to the substrate, and the controller is configured to select a model profile taking into account the estimated object position as a non-variable parameter.

According to an aspect of the invention, there is provided a lithographic cell comprising a lithographic apparatus, a process apparatus and an inspection apparatus, the lithographic cell being configured to measure a property of a substrate, comprising:

a detector configured to receive an actual spectrum signal resulting from radiation diffracted from an object on the substrate;

a controller configured to select a first model profile based on a plurality of variable and non-variable parameters of the model profile from a library of profiles;

a generator configured to generate a first spectrum signal associated with the first model profile; and a comparator configured to compare the first spectrum signal with the actual spectrum signal, wherein if the first spectrum signal and the actual spectrum signal do not match to within a desired tolerance, the generator and comparator are configured to carry out their respective generation and comparison with a second model profile with varied variable parameters, wherein the lithographic apparatus and process apparatus are configured to form a plurality of product layers on the substrate prior to forming the object, and the detector, controller, generator and comparator are configured to measure a parameter of each of the plurality of product layers, and to use the measured parameter to estimate an object position relative to the substrate, and the controller is arranged to select a model profile taking into account the estimated object position as a non-variable parameter.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 2 depicts a first scatterometer;
FIG. 3 depicts a second scatterometer.

DETAILED DESCRIPTION

Figure 1A:
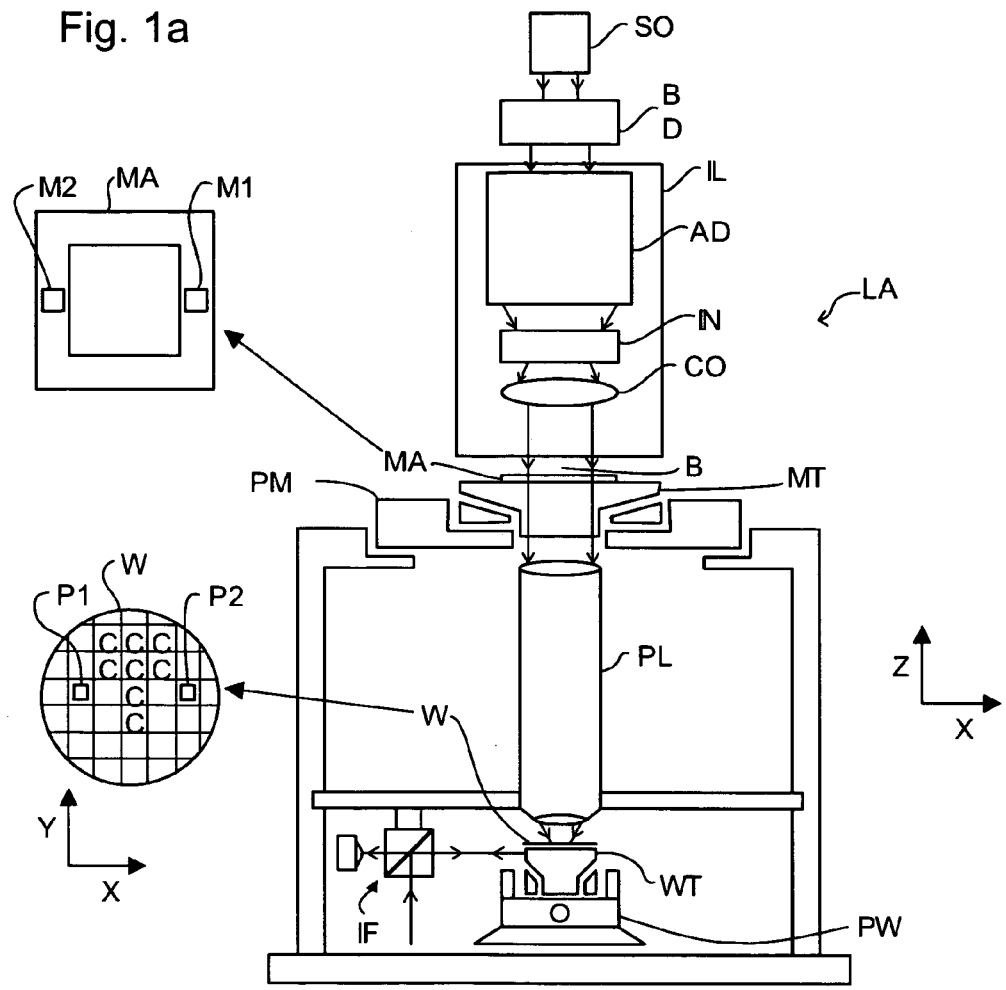
FIG. 1a depicts a lithographic apparatus.

FIG. 1a schematically depicts a lithographic apparatus. The apparatus comprises:

an illumination system (illuminator) IL configured to condition a radiation beam B (e.g. UV radiation or EUV radiation);

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so-called assist features. Generally, the pattern imparted to the radiation beam will correspond to a particular functional layer in a device, such as an integrated circuit, being created in the target portion.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more support structures). In such "multiple stage" machines the additional tables and/or support structures may be used in parallel, or preparatory steps may be carried out on one or more tables and/or support structures while one or more other tables and/or support structures are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1a, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1a) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner), the support structure MT may be connected to a short-stroke actuator only, or it may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 1B:
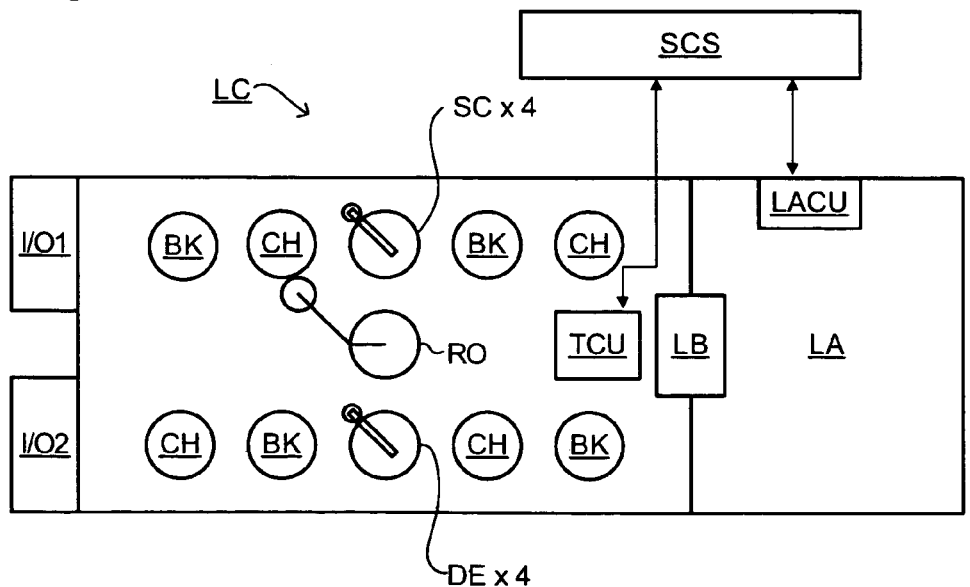
FIG. 1b depicts a lithographic cell or cluster.

As shown in FIG. 1b, the lithographic apparatus LA forms part of a lithographic cell LC, also sometimes referred to as a lithocell or lithocluster, which also includes apparatus to per-form one or more pre- and post-exposure processes on a substrate. Conventionally these include one or more spin coaters SC to deposit a resist layer, one or more developers DE to develop exposed resist, one or more chill plates CH and one or more bake plates BK. A substrate handler, or robot, RO picks up a substrate from input/output ports I/O1, I/O2, moves it between the different process devices and delivers it to the loading bay LB of the lithographic apparatus. These devices, which are often collectively referred to as the track, are under the control of a track control unit TCU which is itself controlled by the supervisory control system SCS, which also controls the lithographic apparatus via lithographic control unit LACU. Thus, the different apparatus may be operated to maximize throughput and processing efficiency.

In order that the substrate that is exposed by the lithographic apparatus is exposed correctly and consistently, it is desirable to inspect an exposed substrate to measure one or more properties such as overlay error between subsequent layers, line thickness, critical dimension (CD), etc. If an error is detected, an adjustment may be made to an exposure of one or more subsequent substrates, especially if the inspection can be done soon and fast enough that another substrate of the same batch is still to be exposed. Also, an already exposed substrate may be stripped and reworked—to improve yield— or discarded—thereby avoiding performing an exposure on a substrate that is known to be faulty. In a case where only some target portions of a substrate are faulty, a further exposure may be performed only on those target portions which are good. Another possibility is to adapt a setting of a subsequent process step to compensate for the error, e.g. the time of a trim etch step can be adjusted to compensate for substrate-to-substrate CD variation resulting from the lithographic process step.

An inspection apparatus is used to determine one or more properties of a substrate, and in particular, how one or more properties of different substrates or different layers of the same substrate vary from layer to layer and/or across a substrate. The inspection apparatus may be integrated into the lithographic apparatus LA or the lithocell LC or may be a stand-alone device. To enable most rapid measurements, it is desirable that the inspection apparatus measure one or more properties in the exposed resist layer immediately after the exposure. However, the latent image in the resist has a very low contrast—there is only a very small difference in refractive index between the part of the resist which has been exposed to radiation and that which has not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibility for rework of a faulty substrate but may still provide useful information, e.g. for the purpose of process control.

FIG. 2 depicts a scatterometer which may be used in an embodiment of the invention. It comprises a broadband (white light) radiation projector 2 which projects radiation onto a substrate W. The reflected radiation is passed to a spectrometer detector 4, which measures a spectrum 10 (i.e. a measurement of intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 2. In general, for the reconstruction, the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another scatterometer that may be used with an embodiment of the invention is shown in FIG. 3. In this device, the radiation emitted by radiation source 2 is focused using lens system 12 through interference filter 13 and polarizer 17, reflected by partially reflective surface 16 and is focused onto substrate W via a microscope objective lens 15, which has a high numerical aperture (NA), desirably at least 0.9 or at least 0.95. An immersion scatterometer may even have a lens with a numerical aperture over 1. The reflected radiation then transmits through partially reflective surface 16 into a detector 18 in order to have the scatter spectrum detected. The detector may be located in the back-projected pupil plane 11, which is at the focal length of the lens 15, however the pupil plane may instead be re-imaged with auxiliary optics (not shown) onto the detector 18. The pupil plane is the plane in which the radial position of radiation defines the angle of incidence and the angular position defines the azimuth angle of the radiation. The detector is desirably a two-dimensional detector so that a two-dimensional angular scatter spectrum (i.e. a measurement of intensity as a function of angle of scatter) of the substrate target can be measured. The detector 18 may be, for example, an array of CCD or CMOS sensors, and may have an integration time of, for example, 40 milliseconds per frame.

A reference beam is often used, for example, to measure the intensity of the incident radiation. To do this, when the radiation beam is incident on the partially reflective surface 16 part of it is transmitted through the surface as a reference beam towards a reference mirror 14. The reference beam is then projected onto a different part of the same detector 18.

One or more interference filters 13 are available to select a wavelength of interest in the range of, say, 405-790 nm or even lower, such as 200-300 nm. The interference filter(s) may be tunable rather than comprising a set of different filters. A grating could be used instead of or in addition to one or more interference filters.

The detector 18 may measure the intensity of scattered radiation at a single wavelength (or a narrow wavelength range), the intensity separately at multiple wavelengths or the intensity integrated over a wavelength range. Further, the detector may separately measure the intensity of transverse magnetic- and transverse electric-polarized radiation and/or the phase difference between the transverse magnetic- and transverse electric-polarized radiation.

Using a broadband radiation source (i.e. one with a wide range of radiation frequencies or wavelengths—and therefore of colors) is possible, which gives a large etendue, allowing the mixing of multiple wavelengths. The plurality of wavelengths in the broadband desirably each has a bandwidth of $\delta\lambda$ and a spacing of at least $2\delta\lambda$ (i.e. twice the wavelength bandwidth). Several "sources" of radiation may be different portions of an extended radiation source which have been split using, e.g., fiber bundles. In this way, angle resolved scatter spectra may be measured at multiple wavelengths in parallel. A 3-D spectrum (wavelength and two different angles) may be measured, which contains more information than a 2-D spectrum. This allows more information to be measured which increases metrology process robustness. This is described in more detail in European patent application publication EP1,628,164A, which document is hereby incorporated in its entirety by reference.

The target on substrate W may be a grating which is printed such that after development, the bars are formed of solid resist lines. The bars may alternatively be etched into the substrate. The target pattern is chosen to be sensitive to a parameter of interest, such as focus, dose, overlay, chromatic aberration in the lithographic projection apparatus, etc., such that variation in the relevant parameter will manifest as variation in the printed target. For example, the target pattern may be sensitive to chromatic aberration in the lithographic projection apparatus, particularly the projection system PL, and illumination symmetry and the presence of such aberration will manifest itself in a variation in the printed target pattern. Accordingly, the scatterometry data of the printed target pattern is used to reconstruct the target pattern. The parameters of the target pattern, such as line width and shape, may be input to the reconstruction process, performed by processing unit PU, from knowledge of the printing step and/or other scatterometry processes.

An embodiment of the present invention relates to the reconstruction of a target object on a substrate W. As discussed above, the cross-sectional shape of the target object is known as its profile. The target object may also be known as a scatterometry object.

For reconstruction purposes, the profile is generally regarded as being made up of a stack of homogenous rectangular cross-section layers and other shapes (such as trapezoids) that form the object. A radiation beam is diffracted from the surface of the scatterometry object, as well as from the surface of other product layers on the substrate. This diffracted beam is detected by a detector that then creates a scatterometry measurement signal from a diffraction pattern. The measurement signal is compared with a calculated signal that is based on a model profile defined by a stack of homogenous layers and shapes. When the calculated signal does not match the measured signal, the model profile is altered so that the associated model signal is more similar to the actual profile of the actual object. This process is continued until the measurement signal and the calculated signal match within acceptable tolerances. Clearly, increasing the number of iterations increases the computation power required to determine the profile of the object. Similarly, increasing the number of parameters that can be altered between comparison steps also increases the required computational power. Above a threshold number of variable parameters, the mathematical reconstruction becomes impossible.

Figure 4A:
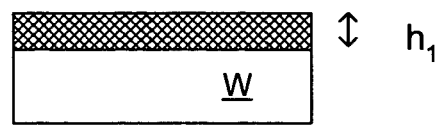
FIGS. 4a, 4b and 4c depict a method according to an embodiment of the invention.

A homogeneous layer such as a product layer, as shown in FIG. 4a on the substrate W, has only a single geometric degree of freedom, which is its thickness $h_1$ (or height from either the substrate surface or the product layer beneath it). The greater the number of product layers between the substrate and the object to be measured, the greater the number of thicknesses $h_n$ and the greater the number of degrees of freedom involved in the reconstruction calculation. The more complicated the reconstruction calculation, the larger the chance of an instable solution and cross-correlation between the different degrees of freedom. By "instable solution", it is assumed that the change in the calculated signal is different for each degree of freedom. In reality, the change in the calculated signal of different geometrical parameters can be similar, which makes it difficult for an optimization algorithm to find the correct solution. For example, if two product layers have a total height hT, increasing the height of the lower product layer by a few nm and at the same time decreasing the height of the upper product layer by a few nm will yield very similar calculated signals (especially if the overall height $h_T$ remains the same). Because the measurement signals are not free of noise, a plurality of measurements of the same target object may result in a wide variety of results. These results are known as instable results. In other words, there is a cross-correlation between parameters or degrees of freedom.

In order to measure a complex stack, e.g. a trapezoid on top of several homogenous layers, a model is made under the assumption that the thicknesses of the homogenous layers are known. The assumption that the thicknesses of underlying layers are constant over the substrate and also known may both be wrong.

Figure 4B:
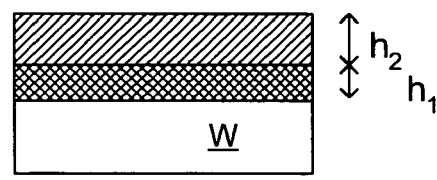
Figure 4C:
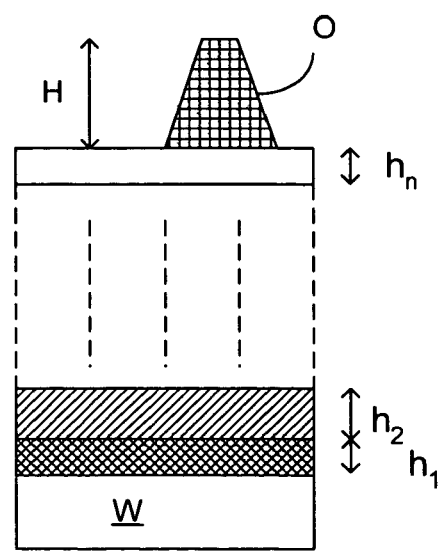

FIGS. 4a, 4b and 4c show how an example complex substrate stack is built layer by layer. Measuring the stack shown in FIG. 4a is straightforward because there is only one degree of freedom, which is the height or thickness of the product layer $h_1$. Measuring the stack shown in FIG. 4b is slightly more difficult because there are two degrees of freedom, namely the layer of the thickness of the first product layer $h_1$ and the thickness of the second product layer $h_2$ on top of the first product layer $h_1$. Finally, measuring the stack shown in FIG. 4c becomes much more difficult as the number of intermediate layers increases. Each product layer thickness $h_1$ to $h_n$ is a separate degree of freedom which results in cross-correlation and bad results if all are assumed to be the same. To add to the complication, one or more of the product layers may also be patterned and have one or more further degrees of freedom within them.

The reason that cross-correlation might occur is that the optimization algorithm that is used to match a model profile with the real profile will carry out this matching using a premise of a specific product layer thickness. The algorithm can assume the product layer thickness in two ways: 1) include the product layer thickness in the optimization process, i.e. have it as a separate variable parameter; or 2) use a fixed value for the product layer thickness. If the fixed value is correct, the optimization algorithm will find the correct profile. However, if the more likely scenario occurs, wherein the fixed value is incorrect, the optimization algorithm will be "distracted" and create an incorrect profile by trying to minimize the difference between the model profile and the actual profile, without having the product layer thickness as an iteratively changeable parameter. The reconstructed profile will therefore likely be unacceptably different from the actual profile. As mentioned above, though, if the product layer thickness is a variable parameter, this introduces a greater number of variables, which may make the optimization routine unnecessarily complicated, if not impossible.

In order to overcome this problem, an embodiment of the present invention includes, in the profile reconstruction method, a step of measuring one or more product layers between the substrate W and the object to be measured O so that the thickness of the one or more product layers may become a known parameter. In the case shown in FIG. 4a, only the thickness $h_1$ needs to be measured. When, in FIG. 4b, a second product layer is placed on the first product layer, the product layer thickness $h_1$ is known (e.g., the measured thickness of the product layer on the substrate is stored in a memory) and so the only unknown degree of freedom is the thickness of the second product layer, $h_2$. As each product layer is added to the stack on the substrate W, the thickness of each new product layer may be measured in turn and so at each step, there is only one degree of freedom that is unknown and to be measured. Finally, as shown in FIG. 4c, if all thicknesses $h_1$ to $h_n$ are known (e.g., the last measured thickness and the previously stored measured thickness(es) may be combined to estimate the position of the object O), the only degrees of freedom that are unknown are those of the object O itself.

In the case of one or more of the product layers being printed layers, the profile of the printed layer(s) may also be more easily determined using the reconstruction technique before a subsequent layer is formed on top of the printed layer.

An advantage of this method is that measuring a single layer on a substrate is far simpler than measuring a stack of differing layers. This is particularly true if the layers have slightly different optical constants. Similarly, trying to model a grating (or other scatterometry object) on a large stack of product layers with unknown thickness may be impossible. Thus, if the one or more layers have been measured prior to the object being introduced to the top of those one or more layers, the result of a large portion of the computation has already been determined and the computation of the model of the object alone may be far simpler.

An advantage of an embodiment of the present invention is that the one or more product layers that are measured may be a homogenous layer(s) or a patterned product layer(s). No previously known scatterometry system may be able to deal with one or more product layers that are patterned (e.g. that contain a scatterometry object or a printed product layer within the measured stack) because the number of degrees of freedom is simply too large to be dealt with mathematically. A benefit of being able to have, for example, multiple patterned product layers is that the scribe lane available for measurement (e.g. alignment and overlay) targets may be greatly increased, as the scribe lanes in more than a single layer can be used for the measurement targets. In other words, if a measurement object that is on top of one or more layers that may also contain a measurement object, all of the layers in the stack can potentially be useful by using the measurement(s) of the lower layer(s).

Figure 5A:
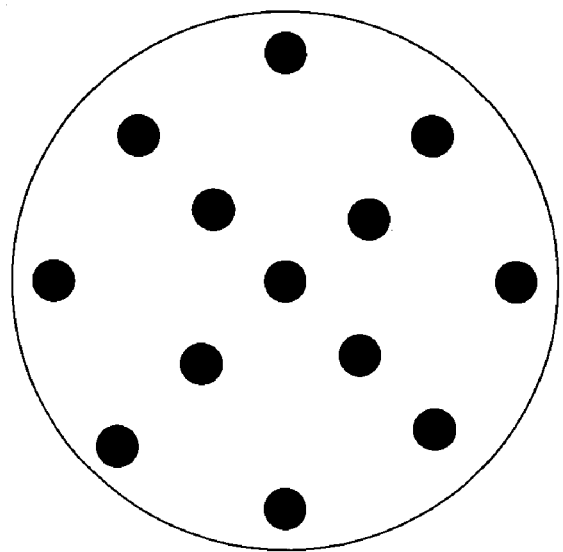
FIGS. 5a and 5b depict measurements sites for diffraction patterns.
Figure 5B:
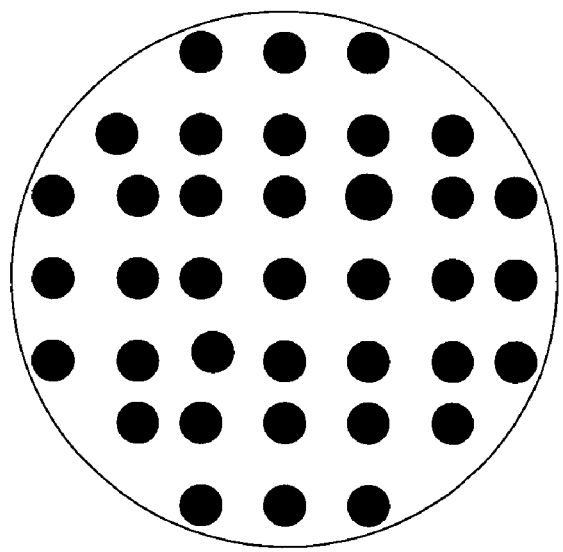

For a homogeneous layer, it is not necessary to measure the complete substrate on all measurement sites, as would be required with a printed patterned layer. It is sufficient to measure the homogeneous layer on a less dense grid such as shown in FIG. 5a, rather than having to measure a diffraction pattern at all of the measurement sites such as shown in FIG. 5b. The measurements taken of the homogeneous layer at the sites shown in FIG. 5a may be used subsequently to extrapolate across the whole substrate W to obtain an estimated thickness of other locations for other sites on the substrate W.

It is also sometimes suitable to measure more than one unknown layer simultaneously, for example if several homogeneous layers are printed subsequently to each other.

Another or alternative advantage of the method described above is that the degrees of freedom of complex stacks may be reduced. More accurate measurement of the profile of a stack on a substrate may therefore be obtained. This is particularly true if there are large numbers of homogenous layers and/or layers with patterns with different pitches or thicknesses in the stack.

This method may be most usefully carried out in a scatterometer positioned as an in-line metrology tool. There is no effect on throughput of the substrate because the substrate passes this scatterometer between pre- and post-exposure processes whether or not one or more product layers are measured and so carrying out the measurement may easily be added to the range of processes that are already carried out without adding too much time. Ultimately, measuring a profile with fewer degrees of freedom more frequently will save time when compared with trying to measure a more complex stack with many degrees of freedom as a final process.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography, a topography of a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A method of reconstructing a shape of an object from a diffraction pattern resulting from radiation illuminating the object, the method comprising:

measuring a thickness of a product layer on a substrate;
using the measured thickness to estimate an object position relative to the substrate, the object positioned on the product layer;
detecting the diffraction pattern of radiation diffracted from the object;
estimating the object shape;

deriving a model diffraction pattern from the estimated shape taking into account the estimated object position;

comparing the model diffraction pattern and the detected diffraction pattern; and determining the actual shape of the object from the difference between the model diffraction pattern and the detected diffraction pattern.

2. The method according to claim 1, wherein the thickness of the product layer is measured on a sparse grid over the substrate.

3. The method according to claim 1, wherein estimating an object position comprises using a modeled product layer thickness at the position of the object to estimate the distance of the object from the substrate.

4. The method according to claim 1, comprising a plurality of product layers on the substrate and wherein each product layer is measured individually.

5. The method according to claim 4, wherein each product layer is measured subsequently to its exposure and, if appropriate, prior to the application of the next product layer.

6. The method according to claim 1, further comprising measuring a variation, over the substrate, of the thickness of the product layer.

7. The method according to claim 1, wherein, in the case of a plurality of subsequent product layers being homogeneous, the plurality of subsequent product layers is measured as a single homogeneous layer.

8. The method according to claim 1, further comprising storing the measured thickness of the product layer on the substrate in a memory and combining the stored measured thickness with a further measured thickness of another product layer on the substrate layer to estimate the object position.

9. An inspection apparatus configured to measure a property of a substrate, the apparatus comprising:

a detector configured to detect an actual spectrum signal associated with an object on the substrate;

a controller configured to select a first model profile based on a plurality of variable and non-variable parameters of the model profile from a library;

a generator configured to generate a first spectrum signal associated with the first model profile; and a comparator configured to compare the first spectrum signal with the actual spectrum signal, wherein if the first spectrum signal and the actual spectrum signal do not match to within a desired tolerance, the generator and comparator are configured to carry out their respective generation and comparison with a second model profile having varied variable profiles with respect to the first model profile, wherein the inspection apparatus is configured to measure a parameter of a product layer on the substrate, and to use the measured parameter to estimate an object position relative to the substrate, and the controller is configured to select a model profile taking into account the estimated object position as a non-variable parameter.

10. The inspection apparatus according to claim 9, wherein the measured parameter of the product layer comprises the thickness of the product layer.

11. The inspection apparatus according to claim 9, wherein the apparatus is configured to store the measured thickness of the product layer on the substrate in a memory and to combine the stored measured thickness with a further measured thickness of another product layer on the substrate layer to estimate the object position.

12. The inspection apparatus according to claim 9, wherein the inspection apparatus is positioned in-line with a lithographic apparatus and process apparatus, together configured to form the product layer on the substrate, and the inspection apparatus is arranged to measure each product layer of a plurality of product layers individually following the respective product layer's formation.

13. A lithographic apparatus comprising an inspection apparatus configured to measure a property of a substrate, the lithographic apparatus comprising:

a detector configured to receive an actual spectrum signal resulting from radiation diffracted from an object on the substrate;

a controller configured to select a first model profile based on a plurality of variable and non-variable parameters of the model profile from a library of profiles;

a generator configured to generate a first spectrum signal associated with the first model profile; and a comparator configured to compare the first spectrum signal with the actual spectrum signal, wherein if the first spectrum signal and the actual spectrum signal do not match to within a desired tolerance, the generator and comparator are configured to carry out their respective generation and comparison with a second model profile having varied variable parameters, wherein the lithographic apparatus is configured to form, in conjunction with a process apparatus, a plurality of product layers on the substrate prior to forming the object, the detector, controller, generator and comparator are configured to measure a parameter of each of the plurality of product layers, and to use the measured parameter to estimate an object position relative to the substrate, and the controller is arranged to select a model profile taking into account the estimated object position as a non-variable parameter.

14. The lithographic apparatus according to claim 13, wherein the measured parameter is a thickness of each of the product layers.

15. A lithographic cell comprising a lithographic apparatus, a process apparatus and an inspection apparatus, the lithographic cell being configured to measure a property of a substrate, comprising:

a detector configured to receive an actual spectrum signal resulting from radiation diffracted from an object on the substrate;

a controller configured to select a first model profile based on a plurality of variable and non-variable parameters of the model profile from a library of profiles;

a generator configured to generate a first spectrum signal associated with the first model profile; and a comparator configured to compare the first spectrum signal with the actual spectrum signal, wherein if the first spectrum signal and the actual spectrum signal do not match to within a desired tolerance, the generator and comparator are configured to carry out their respective generation and comparison with a second model profile with varied variable parameters, wherein the lithographic apparatus and process apparatus are configured to form a plurality of product layers on the substrate prior to forming the object, and the detector, controller, generator and comparator are configured to measure a parameter of each of the plurality of product layers, and to use the measured parameter to estimate an object position relative to the substrate, and the controller is arranged to select a model profile taking into account the estimated object position as a non-variable parameter.

16. The lithographic cell according to claim 15, wherein the measured parameter is a thickness of each of the product layers.

\* \* \* \* \*